United States Patent [19]

O'Phelan et al.

[11] Patent Number: 6,055,455
[45] Date of Patent: *Apr. 25, 2000

[54] FILTERED FEEDTHROUGH FOR AN IMPLANTABLE MEDICAL DEVICE

[75] Inventors: Michael J. O'Phelan, Oakdale; Nick A. Youker, Oak Grove, both of Minn.

[73] Assignee: Cardiac Pacemakers, Inc., St. Paul, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/779,343

[22] Filed: Jan. 6, 1997

[51] Int. Cl.$^7$ .................................................. A61N 1/375
[52] U.S. Cl. ............................................. 607/36; 361/302
[58] Field of Search ................................. 607/9, 36, 37; 361/302

[56] References Cited

U.S. PATENT DOCUMENTS

| | | |
|---|---|---|
| 2,756,375 | 7/1956 | Peck . |
| 3,235,939 | 2/1966 | Rodriquez et al. . |
| 3,690,325 | 9/1972 | Kenny ........................ 607/36 |
| 3,920,888 | 11/1975 | Barr . |
| 4,033,022 | 7/1977 | Currie et al. . |
| 4,148,003 | 4/1979 | Colburn et al. . |
| 4,152,540 | 5/1979 | Duncan et al. . |
| 4,220,813 | 9/1980 | Kyle . |
| 4,247,881 | 1/1981 | Coleman . |
| 4,314,213 | 2/1982 | Wakino . |
| 4,352,951 | 10/1982 | Kyle . |
| 4,362,792 | 12/1982 | Bowsky et al. . |
| 4,421,947 | 12/1983 | Kyle ............................ 607/36 |
| 4,424,551 | 1/1984 | Stevenson et al. . |
| 4,456,786 | 6/1984 | Kyle ............................ 607/36 |
| 4,737,601 | 4/1988 | Gartzke . |
| 4,741,710 | 5/1988 | Hogan et al. . |
| 5,070,605 | 12/1991 | Daglow et al. ............. 607/37 |
| 5,275,620 | 1/1994 | Darby et al. ................. 607/1 |
| 5,333,095 | 7/1994 | Stevenson et al. . |
| 5,531,003 | 7/1996 | Seifried et al. ............. 29/25.42 |
| 5,650,759 | 7/1997 | Hittman et al. ............ 607/37 |
| 5,735,884 | 4/1998 | Thompson et al. ........ 607/36 |
| 5,751,539 | 5/1998 | Stevenson et al. . |
| 5,825,608 | 10/1998 | Duva et al. . |

FOREIGN PATENT DOCUMENTS

| | | | |
|---|---|---|---|
| 0705621 | 4/1996 | European Pat. Off. ....... A61N 1/375 |
| 331959 | 9/1989 | WIPO ..................... 607/36 |

OTHER PUBLICATIONS

"Filters Eliminate EMI Without Cable Disconnection", *Electronic Engineering*, 66, 17, (Sep. 1994).

Makl, S., "EMI Filtering in Medical Implantables", *Medical Device and Diagnostic Industry*, pp. 112–119, (Sep. 1994).

Sarda, I.G., et al., "Ceramic EMI Filters a Review", *Ceramic Bulletin*, 67, pp. 737–746, (Apr. 1988).

Satoh, M., "Filters Add New EMI Dimension to Connectors", *JEE Journal of Electronic Engineering*, 26, pp. 30–32, (Oct. 1, 1989).

*Primary Examiner*—William E. Kamm
*Assistant Examiner*—Carl H. Layno
*Attorney, Agent, or Firm*—Schwegman, Lundberg, Woessner & Kluth, P.A.

[57] ABSTRACT

A cardiac pacing system comprises a pulse generator which includes a housing. Electronics are placed within the housing. Attached to the pulse generator is a lead. The lead has electrodes which are attached to the surface of the heart. The lead carries signals to and from the heart. The electronics use the signals from the heart to make decisions regarding signals to send to the heart to correct for various arrhythmias. A capacitive filter for filtering out electromagnetic interference is positioned on the lead so that unfiltered electromagnetic interference remains outside the housing of the pulse generator. The capacitor can be positioned outside the housing or positioned within a ferrule in an opening of the housing.

46 Claims, 6 Drawing Sheets

FILTERED FEEDTHROUGH FOR AN IMPLANTABLE MEDICAL DEVICE

FIELD OF THE INVENTION

The present invention relates to the field of devices implanted within humans. More particularly, this invention relates to the filter for reducing the effects of electromagnetic interference on the implanted device.

BACKGROUND OF THE INVENTION

Devices implanted in the body for electrical cardioversion or pacing of the heart are well known. More specifically, devices implanted in or about the heart have been used to reverse (i.e., defibrillate or cardiovert) certain life threatening arrhythmias, or to stimulate contraction (pacing) of the heart, where electrical energy is applied to the heart via the electrodes to return the heart to normal rhythm.

Cardiac pacing units are typically comprised of a signal generating unit called a pulse generator and an elongated lead that passes through a vein and into the heart. One end of the lead is attached to the surface of the heart and the other end of the lead is attached to a connection block just outside the pulse generator. An electrode is in the portion of the lead attached to the heart. The electrodes can be used to deliver signals to the heart to defibrillate the heart if its beating too fast or to pace the heart if it is not beating fast enough. The electrodes can also be used to sense certain electrical signals made by the heart to trigger a heart beat. The pulse generator monitors the signals made by the heart and uses this as an input to determine the type of signal needed to be delivered to the heart to correct for an arrhythmia or irregular heart beat.

The lead portion of the cardiac pacing unit is quite long. The lead contains an electrical conductor used to transfer signals from the heart to the pulse generator, and to transfer signals from the pulse generator to the electrodes attached to the heart. The long lead may act like an antennae and is susceptible to stray, external electromagnetic fields which causes noise within the long lead generally called electromagnetic interference ("EMI").

From time to time, humans are subject to external fields which could become problematic to the pulse generator. These fields are broadly known as electromagnetic fields and cause what is broadly known as electromagnetic interference (EMI). This EMI is source generated. Some typical examples of these EMI sources include cellular telephones, anti-theft devices used in department stores, toy cars which are radio controlled, radios and others. In addition, much EMI is generated by sources such as television broadcast antenna, radio stations, satellites and the like. EMI is even caused by electrical current within a typical household.

In certain situations, this EMI can become problematic for the pulse generator. These problems are typically manifest as the device sensing these noise signals as heart signals. When this occurs, the device makes inappropriate therapy delivery decisions and can cause patient harm. More specifically, in the presence of electromagnetic interference or EMI, a signal or signals may be created in a long wire such as the long lead used in a pacing system. The electronics housed within the signal generator of the pacing system generally recognize stray signals or EMI as noise. The possibility exists that EMI produced in the lead and created by an electromagnetic field, may replicate or be close to a signal from the heart. The electronics in the signal generator of the pacing system could misinterpret the EMI as a real signal. If this happens, the result could be disastrous. For example, the signal generator may send a large signal to defibrillate the heart when in fact no such signal is needed.

With more EMI generators being produced every day, it has become increasingly important to filter out this unwanted noise, before the noise gets to device electronics.

The current approach shows the EMI filter capacitor which is located internal to the device and acts as a capacitive filter to high-frequency EMI noise. U.S. Pat. Nos. 4,152,540; 4,424,551; and 5,333,095 are such typical applications of a feedthrough filter. This approach is generally effective but has several drawbacks. One of the drawbacks is that the EMI noise still gets inside the pulse generator. Even though the filter is the first thing the unwanted EMI encounters, it still enters the pulse generator. Depending on the frequency content of the EMI, a portion, or all of the noise could reflect off of the lead prior to being filtered. This renders the capacitor somewhat useless to certain types of EMI. Since new devices are coming on the market daily, it is difficult to anticipate every possible EMI situation.

Another drawback is that allowing space inside the pulse generator for this filter has become inefficient and cumbersome from a mechanical design point of view. This is due to the necessity of allowing a certain amount of headroom inside the device for the capacitive element. In addition, the capacitor is a fairly fragile component such that care must be taken not to damage the component during pulse generator assembly or during the manufacturing process.

During manufacture, a laser weld is used to hermetically close the housing of the pulse generator. The capacitor gets very hot during laser welding and has been known to crack during this process. Such a defect cannot be found until late in the manufacturing process during final electrical testing. Such a crack ruins the entire pulse generator since the outputs short together. Since the pulse generator is a difficult component to inspect, build and control during assembly, it is very expensive to assemble. If such a defect cannot be found until final inspection, the expense associated with assembly is lost.

It is also important to conserve space inside the pulse generator of the pacing system so that a larger battery can be used or a smaller device can be made. Larger batteries generally last longer than smaller batteries. This is important to the person that uses the a pacing system. The pulse generator and the lead is typically implanted in the body of the user. The pulse generator is placed below the skin. When the battery wears out, the batteries are typically "replaced" by replacing the pulse generator. Thus, the longer the battery lasts, the longer the time between surgeries to replace the pulse generator.

SUMMARY OF THE INVENTION

A cardiac pacing system comprises a pulse generator which includes a housing. Electronics are placed within the housing. A feedthrough is used to pass electrical signals from the electronics inside the housing to the connector terminal outside the housing. The connector terminal has an interface which accepts the lead portion of the system. The lead has electrodes which are attached to the surface of the heart. The lead carries signals to and from the heart. The electronics use the signals from the heart to make decisions regarding signals to send to the heart to correct for various arrhythmias. A capacitive filter for filtering out electromagnetic interference is positioned on the wire going into the generator so that unfiltered electromagnetic interference remains outside the housing of the pulse generator. The capacitor can be positioned outside the housing or positioned within a ferrule in an opening of the housing. When positioned outside the housing, the capacitive filter is positioned between the connector terminal and the housing of the pulse generator. The capacitive filter is typically positioned nearer to the housing. The portion of the capacitive filter in contact with bodily fluids can include a covering of a biocompatible material.

The positioning of the capacitive feedthrough filter is very beneficial. In previous arrangements of the feedthrough filter, there was a distinct possibility that unfiltered EMI could enter the housing of the pacing system. The unfiltered EMI could cause the electronics to produce a corrective pulse and send it to the heart, when no such pulse actually needed to be delivered to the heart. When the capacitive feedthrough filter is positioned on the lead so that unfiltered electromagnetic interference remains outside the housing of the pulse generator, the possibility of delivering an unneeded corrective pulse to the heart is substantially lessened or eliminated. In addition, with the capacitive feedthrough filter positioned outside the housing or as part of the ferrule, the capacitor can be tested prior to final assembly of the pulse generator. In addition, the laser weld used to seal the housing will have a lesser effect on the capacitor. Another advantage is that the capacitor does not take up space inside the housing. This space can now be used to house a bigger battery that lasts longer or to reduce the size of the pulse generator itself.

These and other advantages of the invention will become evident as the invention is further described in the description of the preferred embodiments section of the application.

DESCRIPTION OF THE PREFERRED EMBODIMENT

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention. Also, for purposes of illustration, certain portions of the pulse generator may be made larger for the sake of illustrating the invention. For example, the ferrules and the area of the invention are made larger to aid in illustrating the invention. Other portions may be shown symbolically, such as the connector terminal.

Figure 1:
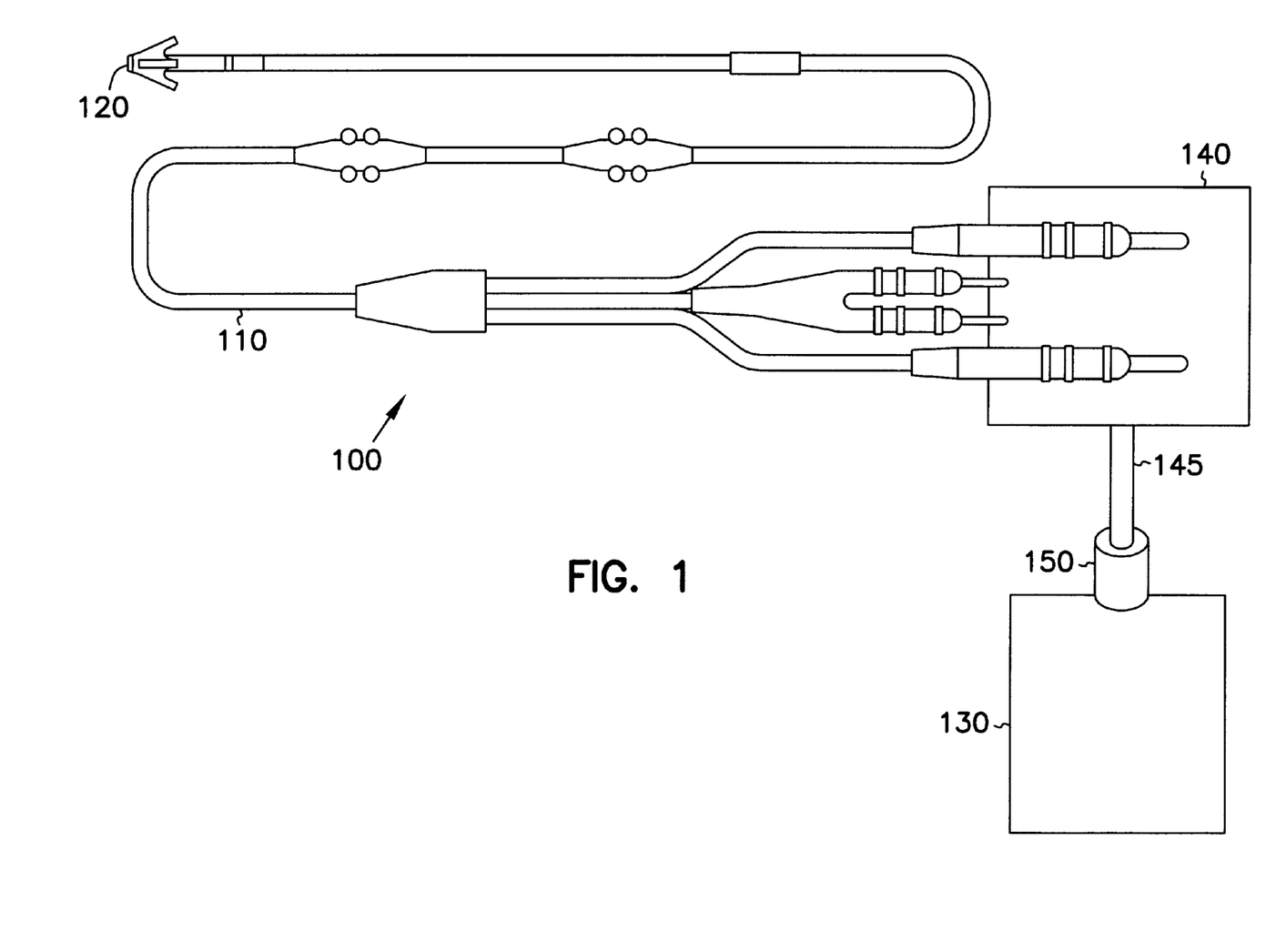
FIG. 1 is a view showing the typical components of an implantable pulse generator system used with the present invention.

FIG. 1 shows a view of a first preferred embodiment of a pacing system for delivering electrical pulses to stimulate the heart. The pacing system 100 is comprised of an elongated lead 110 having electrodes 120 attached to the surface of the heart, and a pulse generator 130 which is used to interpret signals obtained from the heart and to deliver corrective pulses to the heart. The lead 110 interfaces with a connector terminal 140 by way of a feedthrough wire 145. The connector terminal 140 provides for a convenient break in the elongated lead 110. The connector terminal 140 allows the pulse generator 130 to be removed from the remaining portion of the lead. When the pulse generator 130 needs to be replaced, the connector terminal 140 allows for replacement of the pulse generator 130 without having to remove the lead and remove the electrodes 120 from the heart. Also, when the pacing system is first inserted into the patient, most of the lead 110 can be inserted into the body without having to handle the pulse generator 130. This eases the surgeon's task when implanting the pacing system. The lead 110 also has a feedthrough capacitor 150 positioned between the pulse generator 130 and the connector terminal 140.

The elongated lead 110 typically includes a number of helical coil conductors housed within a tubing of biocompatible material, such as silicon polymer. The helical coil conductors provide an electrical connection between the the electrodes 120 at the distal end of the lead which are in electrical contact with the myocardium of the heart, and the pulse generator 130. The electrodes 120 attached to the heart are used to pick up signals from the heart as well as to deliver corrective signals or pulses to the heart. The corrective pulses can be pacing pulses to correct for a slow beating heart (bradycardia condition) or can be defibrillation pulses to correct for a fast beating heart (tachycardia condition). The pulses produced by the heart and sensed by the electrodes 120 are used by the pulse generator 120 to make therapy delivery decisions. The pulse generator contains electronics and a battery power source. The electronics process the signals from the heart and decide the type of corrective pulse and timing of the delivery of that pulse responsive to the signals from the heart.

As mentioned above in the background section of this application, it is critical to remove as much noise as possible from the stream of incoming heart pulses since the results could be disastrous if the noise was misinterpreted by the electronics in the pulse generator 130 as a heart signal requiring corrective action. In the past, EMI or noise generated within the lead by electromagnetic fields has been filtered out using a feedthrough, capacitive filter. Such filters have been positioned within the pulse generator 130.

Figure 2:
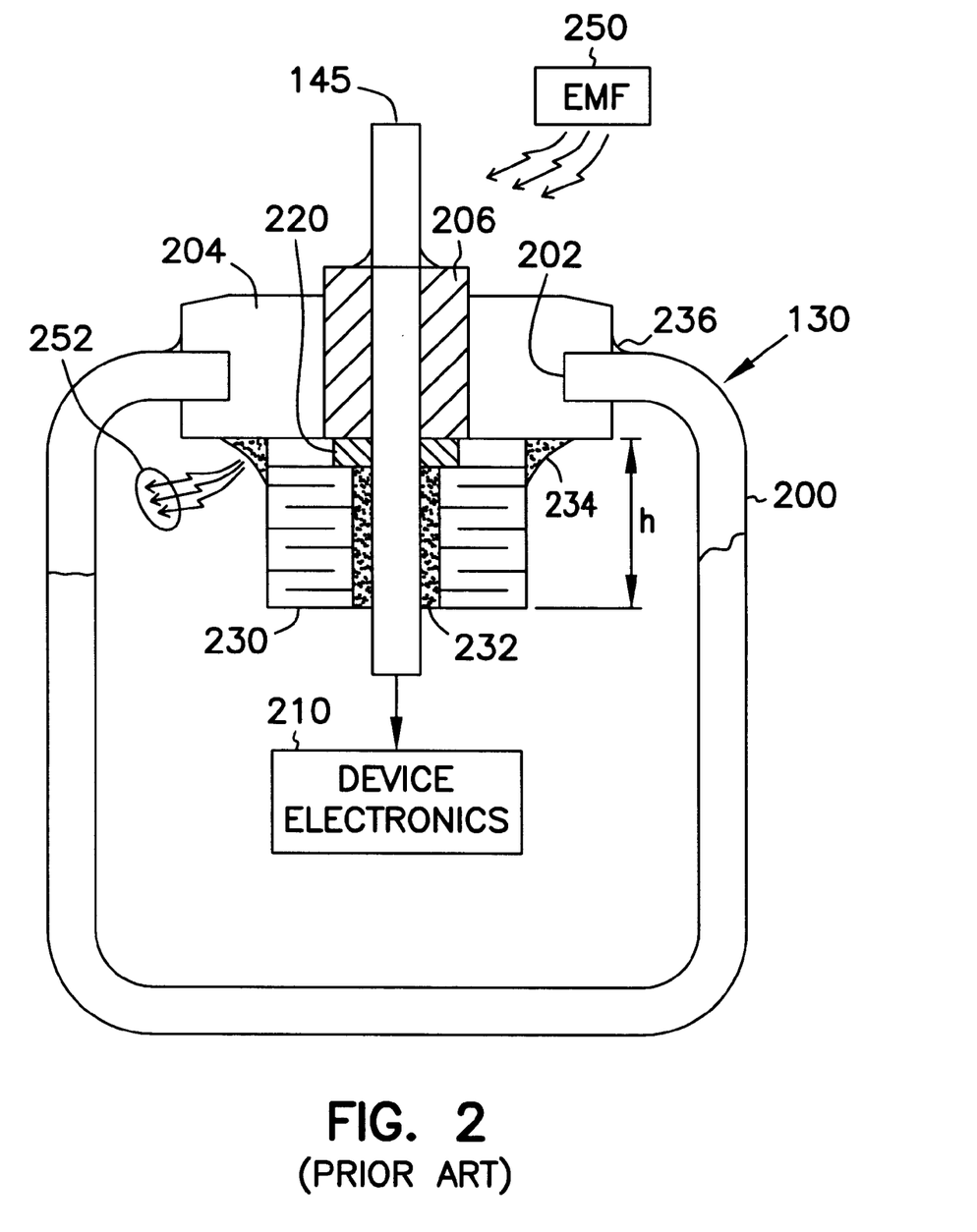
FIG. 2 is a side cutaway view of the pulse generator with a typical filtered feedthrough as used previously.

FIG. 2 shows a typical prior art pulse generator. FIG. 2 also graphically shows the shortcoming associated with the prior art. FIG. 2 is a cutaway portion of the pulse generator 130. The pulse generator includes a housing 200 which has an opening 202 therein. A feedthrough ferrule 204 fits within the opening 202. The feedthrough wire 145 passes through the opening 202 and the feedthrough ferrule 204 and is connected to the device electronics 210 housed within the housing 200. A feedthrough ceramic tube 206 is positioned around the feedthrough wire 145 and in an opening in the feedthrough ferrule 204. Inside the pulse generator 130, there is a polyimide spacer 220 positioned around the lead 110. The polyimide spacer 220 abuts the feedthrough ferrule 204 and the feedthrough ceramic tube 206. A feedthrough capacitor 230 is positioned around the feedthrough wire 145 and abuts the spacer 220. The feedthrough filter capacitor 230 is adhesively attached to the active lead. The adhesive 232 surrounds the lead and is between the feedthrough wire 145 and the feedthrough capacitor 230. The capacitor 230 is also attached to the housing 200 of the pulse generator 130 by way of adhesive attachment 234 between the capacitor 230 and the feedthrough ferrule 204 and by way of the hermetic weld 236 between the ferrule 204 and the housing 200.

The capacitor is set off from the housing 200 as well as from the ferrule 204 by a dimension known as the headroom. The headroom dimension is shown by the dimension h in FIG. 2. The headroom includes the space made by the spacer 220 between the feedthrough ceramic tube 206 and the capacitor 230. This small space, which is part of the headroom, h, is where unfiltered EMI can enter the pulse generator 130. A stray electromagnetic field, shown as box 250 in FIG. 2, can interact with the lead wire 110 and produce EMI or stray noise in the lead 110. The capacitive filter 230, which is positioned inside the housing 200 of the pulse generator 130 can allow some EMI leakage proximate the spacer 220 and the adhesive attachment 234 of the capacitor to the feedthrough ferrule 204. The leakage EMI is depicted as several arrows within a circle which carries the reference numeral 252 in FIG. 2. Depending upon the frequency content of the EMI, a portion or even all of the noise could reflect off the lead prior to it being filtered by the capacitor 230. This renders the capacitor 230 somewhat useless to certain types of EMI. The stray or EMI leakage can affect the electronics 210 and cause them to send an inappropriate pulse or corrective signal down the lead 110 to the heart (not shown). Thus, with the prior art arrangement of the capacitor 230 within the case or housing 200 of the pulse generator 130, there is a distinct possibility that leakage EMI 252 could affect the device electronics 210.

Figure 3:
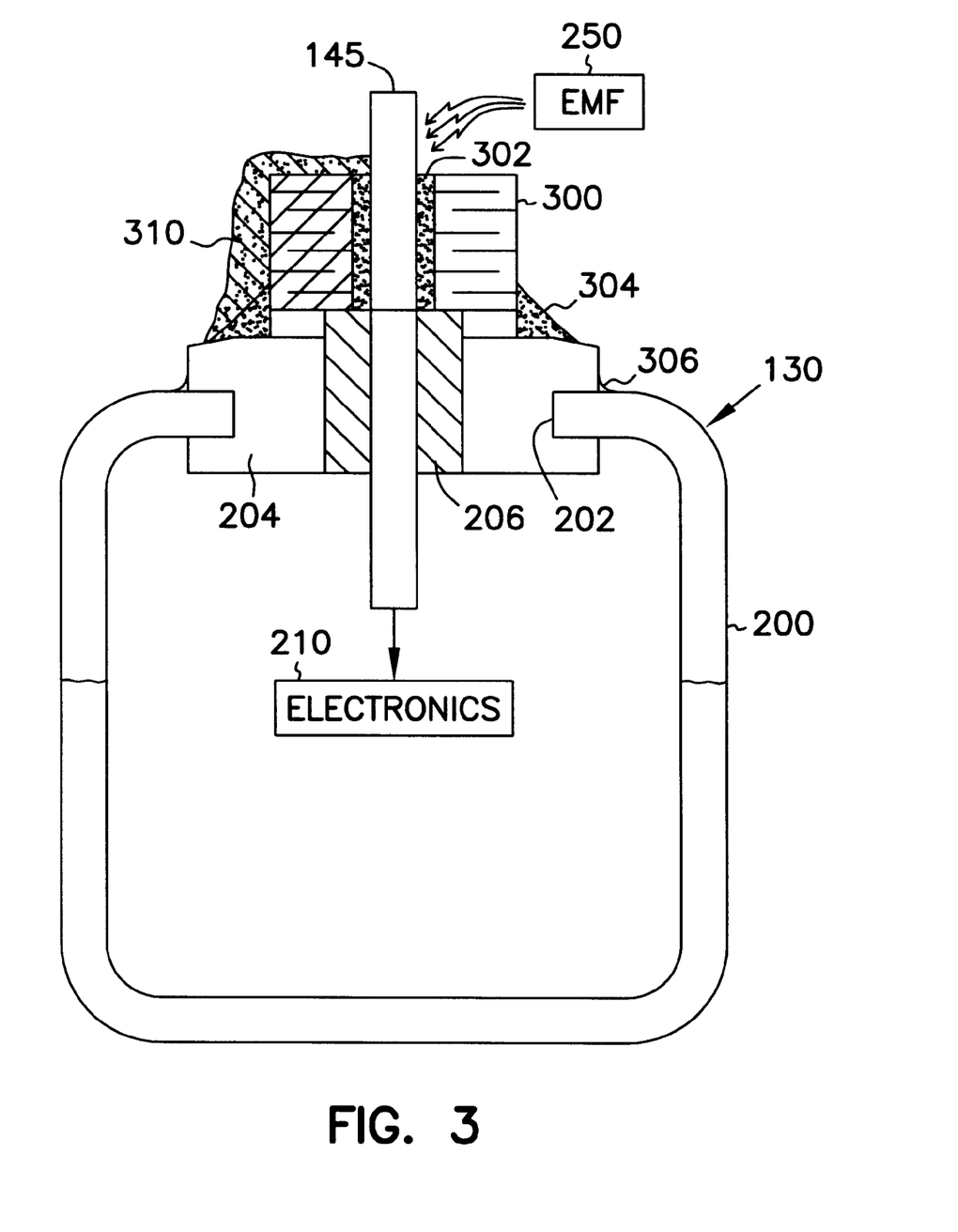
FIG. 3 is a cutaway side view of the pulse generator with one embodiment of the filtered feedthrough.

FIG. 3 shows a cutaway side view of the pulse generator of one preferred embodiment of the invention. It should be noted that components similar with those shown in FIG. 2 carry the same reference numbers as those in FIG. 2. Again, pulse generator 130 includes a housing 200 having an opening 202 therein. A feedthrough ferrule 204 fits within the opening 202. A ceramic feedthrough tube 206 fits around the feedthrough wire 145. The ceramic feedthrough tube 206 fits within the ferrule 204. The feedthrough wire 145 ultimately terminates at the device electronics 210. A feedthrough capacitor 300 is positioned outside the housing 200 of the pulse generator 130. The capacitor 300 can be positioned anywhere along the feedthrough wire 145, however, if the capacitor 300 abuts the ceramic feedthrough tube 206, there will be little or no stray EMF 250 that can enter the feedthrough wire and be unfiltered. In other words, if there is no space between the feedthrough ceramic tube 206 and the capacitor 300, there is no portion of the feedthrough wire 145 which will be exposed to stray EMF 250. The capacitor 300 is attached to the lead by an adhesive 302. The adhesive 302 is electrically conductive and is attached to the active conductors in the lead wire 110 so that a first set of plates is attached to the conductors in the lead 110. Another set of plates of the capacitor 300 are attached to ground or to the housing 200 of the pulse generator 130. This electrical connection is made by an adhesive attachment 304 between the capacitor 300 and the ferrule 204 as well as a hermetic laser weld 306 between the ferrule 204 and the housing 200. The capacitor 300 as well as the adhesive joints such as 302 and 304 are covered or can be covered by a biocompatible material 310 such as silicone polymer, or polyimide.

With this arrangement of the capacitor 300 outside of the housing 200 of the pulse generator 130, the EMI noise never gets inside the pulse generator 130. In other words, the EMI within the feedthrough wire 145 is always or must pass through the filter 300 before entering the housing 200 of the pulse generator 130. The capacitive filter 300 is positioned on the feedthrough wire 145 so that unfiltered electromagnetic interference remains outside the pulse generator 130.

There are also certain other advantages to this arrangement that relate to the manufacture of the pulse generator 130. For example, the capacitor 300 is inspectable following the making of the hermetic laser weld 306. Another manufacturing method possible with this arrangement would be to attach the capacitor 300 to the lead 110 after the laser weld 306 was made. If the device was manufactured in this way, the capacitor 300 would not undergo any sort of heating. A crack in the plates of capacitor 300 would not be caused by the heat of the laser weld. Another advantage is that no spacers are necessary between the capacitor 300 and the feedthrough ferrule 204 or the feedthrough ceramic tube 206. This makes implementation simpler and less expensive. Another large advantage is that with the filter outside of the device, there is no longer a need for headroom. The pulse generator 130 can, therefore, either be downsized or a larger battery, which would last longer, can be housed within the same size housing 200.

Figure 4:
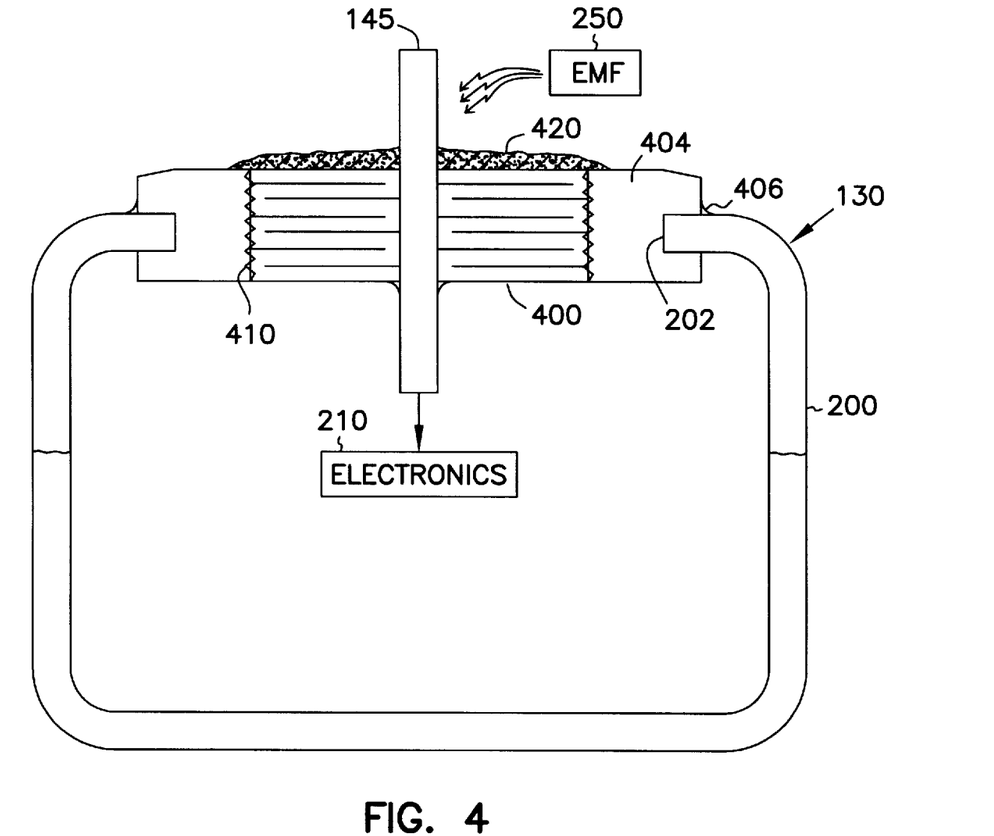
FIG. 4 is a cutaway side view of the pulse generator with another embodiment of the filtered feedthrough.

FIG. 4 shows another preferred embodiment of the invention. FIG. 4 shows a cutaway side view of the pulse generator 130 with this other preferred embodiment of the filter feedthrough. The pulse generator 130 includes a housing 200 having an opening 202. A ferrule 404 fits within the opening 202. The ferrule 404 has an enlarged opening sized to accommodate filter feedthrough capacitor 400. The feedthrough wire 145 passes through the capacitor to the inside of the housing 200 where it is ultimately connected to the device electronics 210. Thus, in this embodiment of the invention, the ferrule 404 and the capacitor 400 are combined. The capacitor 400 is still positioned on the lead so that unfiltered electromagnetic interference 250 remains outside the housing 200 of the pulse generator 130. The capacitor 400 has multiple sets of plates. One set of plates is attached to ground or to the housing 200 of the pulse generator 130. This attachment is accomplished by a gold alloy braze or any other suitable brazing alloy 410 between the capacitor 400 and the ferrule 404. A hermetic laser weld 406 is made between the ferrule 404 and the housing 200 to complete the electrical connection between the first set of plates in the capacitor and the housing 200. The second set of plates is attached to the feedthrough wire 145. A second braze 412 attaches the lead to the second set of plates of the capacitor 400. A biocompatible material 420 such as silicone polymer, or polyimide, can be placed upon the capacitor along the surface which would be exposed to bodily fluid when the pulse generator 130 is implanted into a human.

Again, there are many advantages associated with this preferred embodiment of the invention. The chief advantage is that the capacitive filter is positioned on the feedthrough wire so that unfiltered electromagnetic interference 250 remains outside the housing 200 of the pulse generator 130. As a result of this positioning of the capacitor, EMI noise that is unfiltered will not get into the inside of the housing 200. This minimizes the chances of the electronics receiving false signals that are created by stray electromagnetic fields. An additional advantage is that the capacitor is inspectable after the laser weld during manufacture. The laser weld 406 hermetically seals the opening 202 in the housing 200 of the pulse generator 130. In addition, this implementation is less expensive to manufacture since many of the parts have been eliminated. Yet another advantage is that there is no headroom required inside of the device since the capacitor 400 is integrated with the ferrule 404. The result is that there is more room available inside the housing 200 so that a larger battery can be used for a longer lasting pulse generator. The other option is that the housing 200 could be downsized. In addition, with this particular preferred embodiment, it is less cumbersome since there is no capacitor on the outside of the pulse generator 130.

Figure 5:
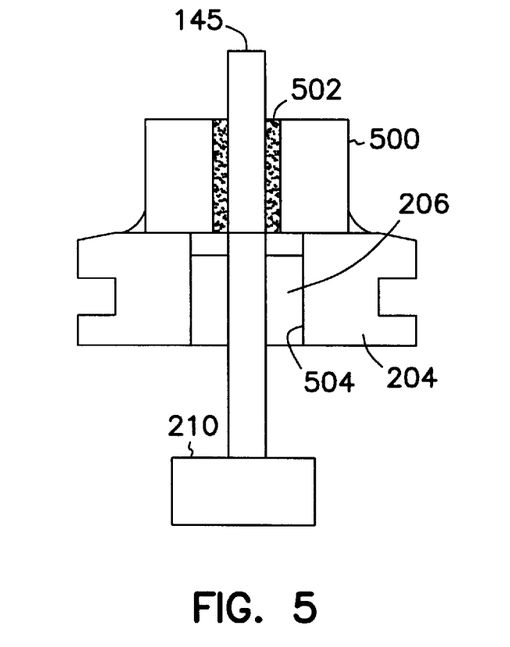
FIG. 5 is a cutaway side view of a ferrule for a pulse generator showing another embodiment of the filtered feedthrough.

FIG. 5 is a cutaway side view of a ferrule 204 for a pulse generator showing another embodiment of the filtered feedthrough. In this particular embodiment, the ferrule 204 has an opening 504 therein. A ceramic feedthrough tube 206 fits within the opening 504 and the ferrule 204. The feedthrough wire 145 fits within the ceramic feedthrough tube 206. A capacitor 500 fits on the ferrule 204. It should be noted that there is a space between the ceramic feedthrough tube 206 and the capacitor 500. The feedthrough wire 145 fits through the capacitor 500 and is attached to the capacitor by electrically conductive adhesive 502. The feedthrough wire passes from the connector terminal (not shown in this figure) to the electronics 210 within the housing of the pulse generator. It is worthy to note that in this embodiment, the ceramic feedthrough tube 206 does not, but could abut the capacitor 500. Stray electromagnetic interference is filtered before it enters the housing of the pulse generator to prevent EMI within the housing of the pulse generator.

Figure 6:
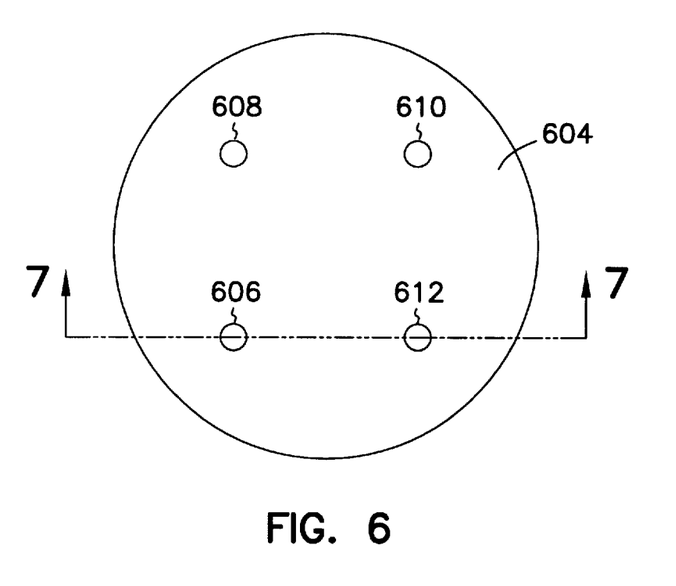
FIG. 6 is a top view of a ferrule for a pulse generator from an embodiment of the filtered feedthrough for multiple feedthroughs.
Figure 7:
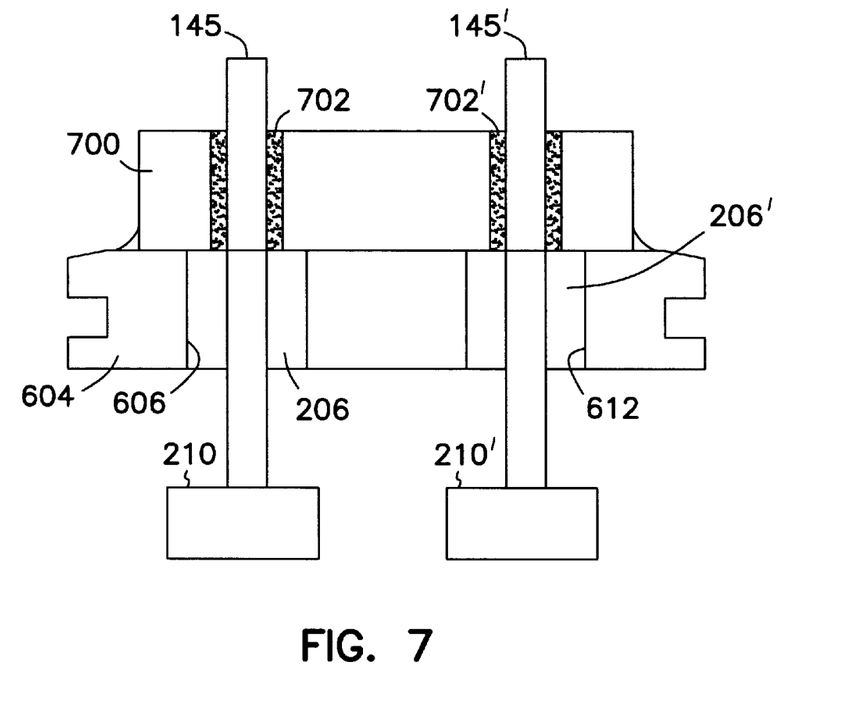
FIG. 7 is a cutaway side view of the ferrule shown in FIG. 6 with multiple feedthroughs placed therein.
Figure 8:
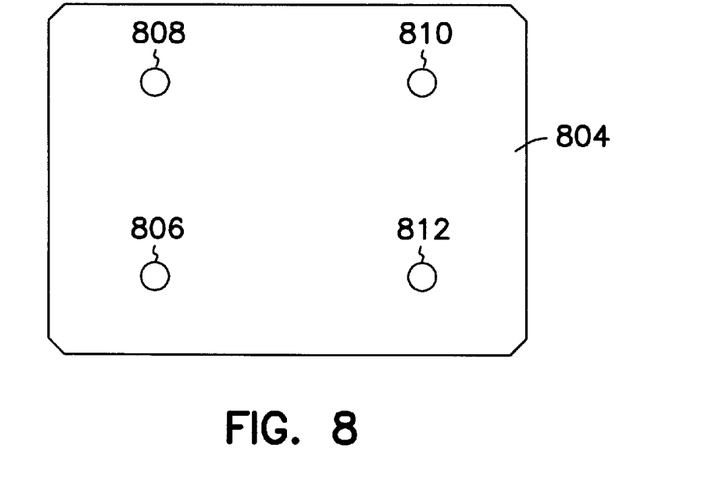
FIG. 8 is a top view of another ferrule for multiple feedthroughs.

FIGS. 6, 7 and 8 show that there also embodiments that allow for multiple feedthrough wires 145. For example, FIG. 6 shows a ferrule 604 which has four openings 606, 608, 610 and 612 therein. It should be noted that there may be as few as one feedthrough wire 145 for a particular application or there may be as many as six feedthrough wires 145 in other applications. The particular arrangement shown in FIG. 6 allows for four feedthrough wires 145 passing through each of the openings 606, 608, 610 and 612 in the ferrule 604.

FIG. 7 is a cutaway side view of the ferrule 604 shown in FIG. 6 having multiple feedthrough wires 145 and 145' placed within the openings in the ferrule 604. FIG. 7 is taken along cut line 7—7 from FIG. 6. As a result, the two openings 606 and 612 in the ferrule are the only ones shown. A ceramic feedthrough tube 206 fits within the opening 606. The ceramic feedthrough tube 206 fits around the feedthrough wire 145. Similarly, a ceramic tube 206' fits around feedthrough wire 145'. The ceramic tube 206' fits within the opening 612 in the ferrule 604. Each of the feedthrough wires 145 and 145' are attached to electronics 210 and 210' within the housing of the pulse generator. It should be noted that the electronics 210 and 210' can be the same set of electronics or can be a different set of electronics or even different portions of a same electrical component. Adjacent the ferrule 604 is a capacitor 700 which has multiple openings therein. The capacitor 700 is attached to the feedthrough wire 145 by electrically conductive adhesive 702. More specifically, the capacitor has a first set of plates and a second set of plates and one of the sets of plates of the capacitor is attached to the feedthrough wire 145 by the electrically conductive adhesive 702. Similarly, the same set of plates of the capacitor 700 is attached to the feedthrough wire 145' by the electrically conductive adhesive 702'. The other set of plates not connected to one of the feedthrough wires 145 or 145' is attached to the housing (not shown in FIG. 7). The capacitor is positioned so that stray electromagnetic fields do not produce EMI within the housing of the pulse generator. In other words, no unfiltered portion of the lead 145 is presented within the housing of the pulse generator.

FIG. 8 also shows another ferrule 804 which has multiple openings 806, 808, 810, and 812 therein. In this particular embodiment, the ferrule is rectangularly shaped. It should be noted that the ferrule can take on most any shape and can house or have openings for as many feedthrough wires 145 as desired for the particular application.

The advantages are numerous as set forth above. It should be noted that in each of the preferred embodiments described herein, the capacitor is positioned so that no unfiltered EMI enters the inside of the housing of the pulse generator. This is the chief advantage of both of these preferred embodiments. This advantage is very important to patients since it minimizes the possibility that stray electromagnetic fields could produce electromagnetic interference in the lead and that electromagnetic interference could get inside of the pulse generator 130 and affect the electronics 210. The worst possible scenario would be that the stray EMI inside the pulse generator might cause the electronics to send a defibrillation signal to the heart when in fact it is not needed. With the preferred embodiment shown herein, this possibility is minimized, if not eliminated.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A cardiac pacing system, comprising:
    a pulse generator including a housing and electronics within the housing;
    a lead attached to said pulse generator; and
    a capacitive filter for filtering out electromagnetic interference, said capacitive filter mounted outside of the housing of the pulse generator and connected to the lead to substantially reduce electromagnetic interference entering the housing.

2. The cardiac pacing system of claim 1, wherein the capacitive filter is substantially covered with a biocompatible material.

3. The cardiac pacing system of claim 2, wherein the housing of the pulse generator has an opening therein, the housing further comprising a ferrule positioned within an opening of the housing, the ferrule including a capacitive filter.

4. The cardiac pacing system of claim 3, wherein a surface of the capacitive filter exposed to bodily fluids is substantially covered with a biocompatible material.

5. The cardiac pacing system of claim 1, wherein the capacitive filter comprises:
    a first set of plates electrically connected to the housing of the pulse generator; and
    a second set of plates electrically connected to the lead.

6. The cardiac pacing system according to claim 1, wherein the housing further comprises a ferrule, the ferrule including the capacitive filter.

7. The cardiac pacing system according to claim 6, wherein the ferrule is attached to the housing with a weld and the capacitor is attached to the ferrule with adhesive.

8. The cardiac pacing system according to claim 6, wherein at least one surface of the capacitor is mounted against the ferrule.

9. The cardiac pacing system according to claim 8, wherein the at least one surface comprises a bottom surface of the capacitor.

10. The cardiac pacing system according to claim 6, wherein the ferrule comprises a square-shaped ferrule.

11. A capacitor for use as a feedthrough filter for a heart pacing device and adapted for implantation in a human body, said capacitor comprising:

a first set of one or more plates; and a second set of one or more plates spaced away from the first set of plates; and a capacitor housing having said first set of plates and said second set of plates positioned therein, said housing comprising a biocompatible material.

12. The capacitor of claim 11 wherein the outside of the housing is substantially encapsulated within a biocompatible material.

13. A lead portion adapted for connection to a pulse generator of a pacing system, said lead portion comprising:

a conductor having a first end and a second end;

a connector terminal connected to one of said first or second ends, the other of said first or second ends adapted to connect to the pulse generator; and a capacitor electrically connected to the conductor and a housing of the pulse generator and positioned on the lead portion outside of the housing of the pulse generator such that electromagnetic interference remains substantially outside the housing of the pulse generator.

14. The lead portion of claim 13, further comprising an elongate lead having electrodes positioned in the heart for receipt and delivery of signals to the heart and which is adapted for implantation within a human body.

15. A cardiac pacing system, comprising:

a pulse generator further comprising a housing and electronics within the housing;

a lead attached to said pulse generator; and a capacitive filter positioned outside of the housing of the pulse generator on the lead attached to the pulse generator.

16. The cardiac pacing system of claim 15, further comprising a connector terminal positioned outside of the housing of the pulse generator, said capacitive filter positioned between the housing of the pulse generator and the connector terminal.

17. An implantable device, comprising:

a pulse generator including a housing and electronics within the housing, the housing having an opening; and a filtered feedthrough, including:

a feedthrough wire providing an electrical connection to the electronics, the electrical connection external to the housing; and a capacitor adapted to substantially seal an opening in the housing, the capacitor electrically connected to the housing and electrically connected to the feedthrough wire to substantially prevent electromagnetic interference from interfering with the electronics.

18. The implantable device of claim 17, wherein the capacitor comprises a first set of plates attached to the housing and a second set of plates attached to the feedthrough wire.

19. The implantable device of claim 17, wherein the opening comprises a ferrule with an inner diameter which substantially conforms to an outer diameter of the capacitor.

20. The implantable device of claim 17, wherein the opening comprises a ferrule having an inner diameter which is smaller than the outer diameter of the capacitor and wherein the capacitor is attached to the ferrule.

21. The implantable device of claim 17, wherein the capacitor includes an aperture for the feedthrough wire.

22. The implantable device of claim 17, wherein a surface of the capacitor exposed to bodily fluids is substantially covered with a biocompatible material.

23. The cardiac pacing system according to claim 1, further comprising a feedthrough wire providing an interface to the lead and an electrical connection to the electronics, the electrical connection external to the housing, the filter adapted to substantially seal an opening in the housing, and the filter electrically connected to the housing and electrically connected to the feedthrough wire to substantially prevent electromagnetic interference from interfering with the electronics.

24. The cardiac pacing system according to claim 23, wherein the filter comprises a capacitor having a first set of plates attached to the housing and a second set of plates attached to the feedthrough wire.

25. The cardiac pacing system according to claim 23, wherein the opening comprises a ferrule with an inner diameter which substantially conforms to an outer diameter of the filter.

26. The cardiac pacing system according to claim 23, wherein the opening comprises a ferrule having an inner diameter which is smaller than the outer diameter of the filter and wherein the filter is attached to the ferrule.

27. The cardiac pacing system according to claim 23, wherein the filter includes an aperture for the feedthrough wire.

28. The cardiac pacing system according to claim 23, wherein a surface of the filter exposed to bodily fluids is substantially covered with a biocompatible material.

29. An implantable device, comprising:

a pulse generator including a housing;

electronics disposed within the housing;

a filtered feedthrough including a feedthrough wire and a capacitor;

the feedthrough wire providing an electrical connection to the electronics, the electrical connection external to the housing;

the capacitor electrically connected to the housing and electrically connected to the feedthrough wire to substantially prevent electromagnetic interference from interfering with the electronics; and the capacitor mounted outside of the housing of the pulse generator.

30. The implantable device according to claim 29, further comprising multiple feedwires.

31. The implantable device according to claim 29, wherein at least four feedthrough wires provide an electrical connection to the electronics.

32. The implantable device according to claim 29, wherein the capacitor is attached to the feedthrough wire with electrically conductive adhesive.

33. The implantable device according to claim 29, the housing further comprising a ferrule, wherein a ceramic feedthrough tube fits within an opening in the ferrule, and the ceramic feedthrough tube fits around the feedthrough wire.

34. A cardiac pacing system, comprising:

a pulse generator including a housing and electronics within the housing;

a lead attached to said pulse generator;

a capacitive filter for filtering out electromagnetic interference, said capacitive filter mounted outside of the housing of the pulse generator and connected to the lead to substantially reduce electromagnetic interference entering the housing; and wherein the capacitive filter is substantially covered with a biocompatible material.

35. A cardiac pacing system, comprising:

a pulse generator including a housing and electronics within the housing;

a lead attached to said pulse generator;

a capacitive filter for filtering out electromagnetic interference, said capacitive filter mounted outside of the housing of the pulse generator and connected to the lead to substantially reduce electromagnetic interference entering the housing; and wherein the housing of the pulse generator has an opening therein, the housing further comprising a ferrule positioned within an opening of the housing, the ferrule including a capacitive filter.

36. The cardiac pacing system of claim 35, wherein a surface of the capacitive filter exposed to bodily fluids is substantially covered with a biocompatible material.

37. A cardiac pacing system, comprising:

a pulse generator including a housing and electronics within the housing;

a lead attached to said pulse generator;

a capacitive filter for filtering out electromagnetic interference, said capacitive filter mounted outside of the housing of the pulse generator and connected to the lead to substantially reduce electromagnetic interference entering the housing; and the capacitive filter comprising a first set of plates electrically connected to the housing of the pulse generator; and a second set of plates electrically connected to the lead.

38. A cardiac pacing system, comprising:

a pulse generator further comprising a housing and electronics within the housing;

a lead attached to said pulse generator;

a capacitive filter positioned outside of the housing of the pulse generator on the lead attached to the pulse generator; and a connector terminal positioned outside of the housing of the pulse generator, said capacitive filter positioned between the housing of the pulse generator and the connector terminal.

39. An implantable device, comprising:

a pulse generator including a housing and electronics within the housing, the housing having an opening; and a filtered feedthrough, including:

a feedthrough wire providing an electrical connection to the electronics, the electrical connection external to the housing; and a capacitor adapted to substantially seal an opening in the housing, the capacitor electrically connected to the housing and electrically connected to the feedthrough wire to substantially prevent electromagnetic interference from interfering with the electronics;

wherein the capacitor comprises a first set of plates attached to the housing and a second set of plates attached to the feedthrough wire.

40. A cardiac pacing system, comprising:

a pulse generator including a housing and electronics within the housing;

a lead attached to said pulse generator;

a capacitive filter for filtering out electromagnetic interference, said capacitive filter mounted outside of the housing of the pulse generator and connected to the lead to substantially reduce electromagnetic interference entering the housing;

a feedthrough wire providing an interface to the lead and an electrical connection to the electronics, the electrical connection external to the housing, the filter adapted to substantially seal an opening in the housing, and the filter electrically connected to the housing and electrically connected to the feedthrough wire to substantially prevent electromagnetic interference from interfering with the electronics; and wherein the filter comprises a capacitor having a first set of plates attached to the housing and a second set of plates attached to the feedthrough wire.

41. A cardiac pacing system, comprising:

a pulse generator including a housing and electronics within the housing;

a lead attached to said pulse generator;

a capacitive filter for filtering out electromagnetic interference, said capacitive filter mounted outside of the housing of the pulse generator and connected to the lead to substantially reduce electromagnetic interference entering the housing;

a feedthrough wire providing an interface to the lead and an electrical connection to the electronics, the electrical connection external to the housing, the filter adapted to substantially seal an opening in the housing, and the filter electrically connected to the housing and electrically connected to the feedthrough wire to substantially prevent electromagnetic interference from interfering with the electronics; and wherein the opening comprises a ferrule having an inner diameter which is smaller than the outer diameter of the filter and the filter is attached to the ferrule.

42. A cardiac pacing system, comprising:

a pulse generator including a housing and electronics within the housing;

a lead attached to said pulse generator;

a capacitive filter for filtering out electromagnetic interference, said capacitive filter mounted outside of the housing of the pulse generator and connected to the lead to substantially reduce electromagnetic interference entering the housing;

the housing further comprises a ferrule, the ferrule including the capacitive filter, wherein at least one surface of the capacitor is mounted against the ferrule, and the at least one surface comprises a bottom surface of the capacitor.

43. A cardiac pacing system, comprising:

a pulse generator including a housing and electronics within the housing;

a lead attached to said pulse generator;

a capacitive filter for filtering out electromagnetic interference, said capacitive filter mounted outside of the housing of the pulse generator and connected to the lead to substantially reduce electromagnetic interference entering the housing;

the housing further comprises a ferrule, the ferrule including the capacitive filter, wherein the ferrule comprises a square-shaped ferrule.

44. An implantable device, comprising:

a pulse generator including a housing;

electronics disposed within the housing;

a filtered feedthrough including a feedthrough wire and a capacitor;

the feedthrough wire providing an electrical connection to the electronics, the electrical connection external to the housing;

the capacitor electrically connected to the housing and electrically connected to the feedthrough wire to substantially prevent electromagnetic interference from interfering with the electronics;

the capacitor mounted outside of the housing of the pulse generator; and wherein at least four feedthrough wires provide an electrical connection to the electronics.

45. An implantable device, comprising:

a pulse generator including a housing;

electronics disposed within the housing;

a filtered feedthrough including a feedthrough wire and a capacitor;

the feedthrough wire providing an electrical connection to the electronics, the electrical connection external to the housing;

the capacitor electrically connected to the housing and electrically connected to the feedthrough wire to substantially prevent electromagnetic interference from interfering with the electronics;

the capacitor mounted outside of the housing of the pulse generator; and wherein the capacitor is attached to the feedthrough wire with electrically conductive adhesive.

46. An implantable device, comprising:

a pulse generator including a housing;

electronics disposed within the housing;

a filtered feedthrough including a feedthrough wire and a capacitor;

the feedthrough wire providing an electrical connection to the electronics, the electrical connection external to the housing;

the capacitor electrically connected to the housing and electrically connected to the feedthrough wire to substantially prevent electromagnetic interference from interfering with the electronics;

the capacitor mounted outside of the housing of the pulse generator; and the housing further comprising a ferrule, wherein a ceramic feedthrough tube fits within an opening in the ferrule, and the ceramic feedthrough tube fits around the feedthrough wire.

* * * * *